United States Patent
Scampini

(10) Patent No.: US 7,300,163 B2
(45) Date of Patent: Nov. 27, 2007

(54) SLIDE MISLOAD DETECTION SYSTEM AND METHOD

(75) Inventor: Steven A. Scampini, Boston, MA (US)

(73) Assignee: Cytyc Corporation, Marlborough, MA (US)

( * ) Notice: Subject to any disclaimer, the term of this patent is extended or adjusted under 35 U.S.C. 154(b) by 180 days.

(21) Appl. No.: 11/040,958

(22) Filed: Jan. 21, 2005

(65) Prior Publication Data

US 2006/0164611 A1    Jul. 27, 2006

(51) Int. Cl.
*G03B 23/00* (2006.01)
*G01B 11/00* (2006.01)

(52) U.S. Cl. .................... 353/103; 356/400

(58) Field of Classification Search .......... 353/103; 356/247, 400
See application file for complete search history.

(56) References Cited

U.S. PATENT DOCUMENTS

| | | | |
|---|---|---|---|
| 3,134,839 A | | 5/1964 | Girotti |
| 3,334,540 A | * | 8/1967 | Wright .................. 353/22 |
| 3,912,360 A | | 10/1975 | Beckel |
| 4,432,618 A | | 2/1984 | Parker et al. |
| 5,302,982 A | * | 4/1994 | Davis .................. 353/30 |
| 5,488,494 A | | 1/1996 | Redfiled et al. |
| 5,588,555 A | | 12/1996 | Kanamori et al. |
| 5,690,892 A | | 11/1997 | Babler et al. |
| 6,362,883 B1 | * | 3/2002 | Watkins ............... 356/399 |
| 7,140,738 B2 | * | 11/2006 | Guiney et al. ........... 353/103 |

| | | |
|---|---|---|
| 2003/0099580 A1 | 5/2003 | Pressman et al. |
| 2004/0071327 A1 | 4/2004 | Ellis et al. |

FOREIGN PATENT DOCUMENTS

| | | |
|---|---|---|
| EP | 0 377 503 | 7/1990 |
| WO | WO 02/37158 | 5/2002 |

OTHER PUBLICATIONS

PCT International Search Report for PCT/US2005/046290, Applicant: Cytyc Corporation, Forms PCT/ISA/210 and 220, dated May 29, 2005 (6 pages).
PCT Written Opinion of the International Search Authority for PCT/US2005/046290, Applicant: Cytyc Corporation., Form PCT/ISA/237, dated May 29, 2005 (7 pages).

* cited by examiner

*Primary Examiner*—Christopher Mahoney
(74) *Attorney, Agent, or Firm*—Vista IP Law Group LLP

(57) ABSTRACT

A system and method for determining whether one or more slides are loaded properly within a cassette. Each slide includes one or more transparent regions and one or more non-transparent regions. The slides are between a light source and a sensor. The light source generates light that is directed towards the sensor through the slides. If the sensor is able to detect light from the light source, then the slides are properly loaded in the cassette. Slides are not properly loaded if the light is blocked by a non-transparent region before reaching the sensor. The sensor or a separate controller can generate a signal or data to provide an indication to a user or to processing equipment that the slides are or are not properly loaded. For example, a speaker or an indicator light can be used to provide an indication to the user. The signal or data can also be used for other functions, such as displaying a message on a screen indicating whether the slides are properly loaded.

37 Claims, 8 Drawing Sheets

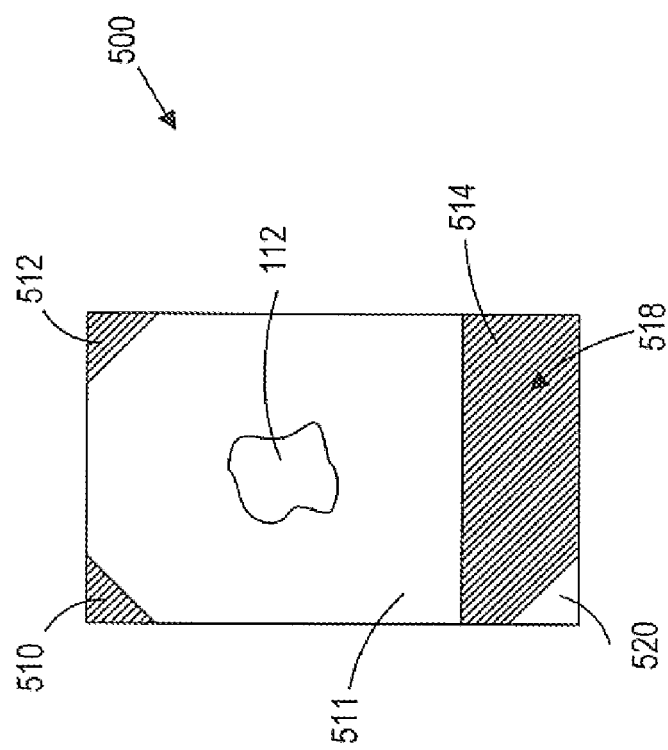

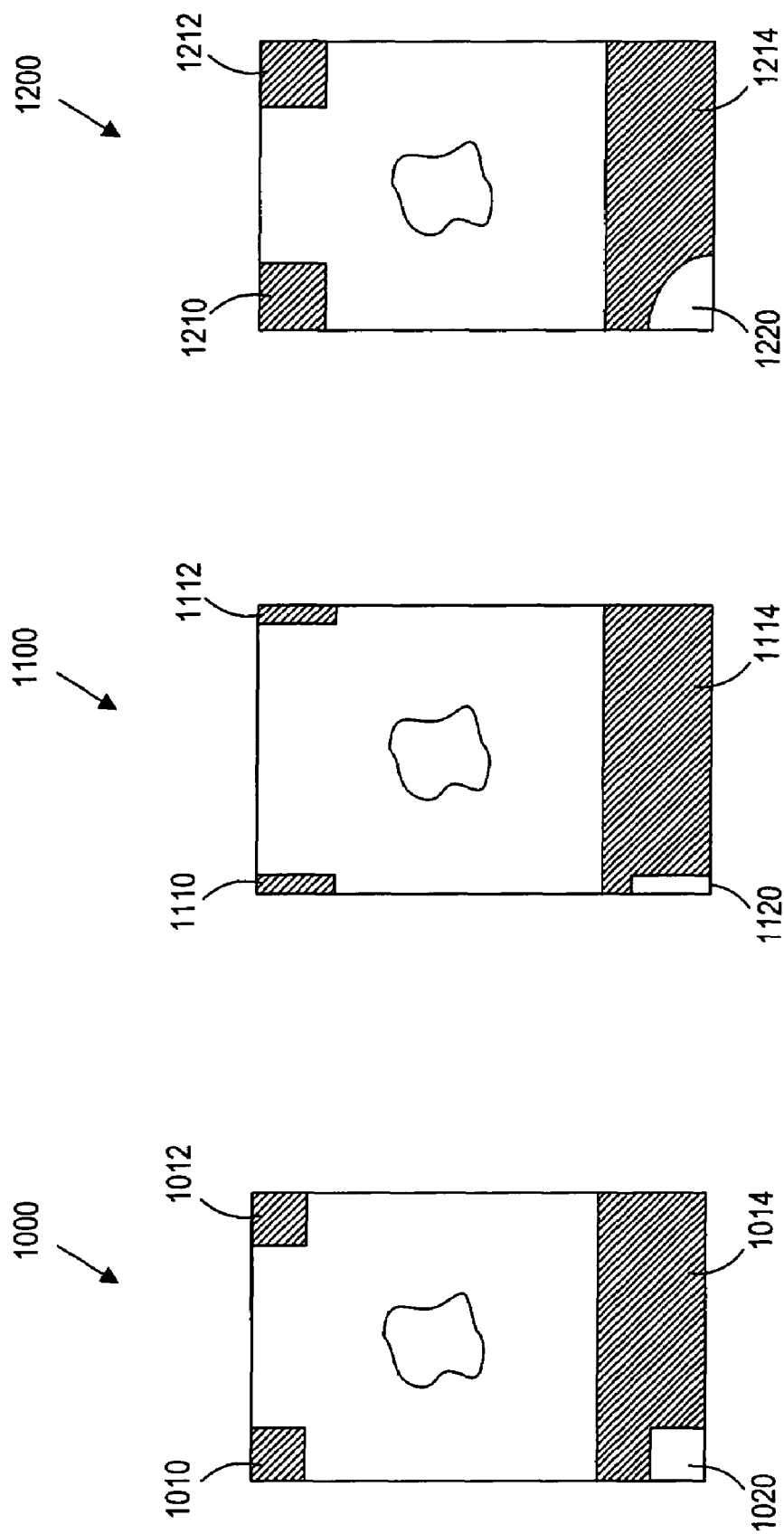

SLIDE MISLOAD DETECTION SYSTEM AND METHOD

FIELD OF THE INVENTION

The present invention relates to slide storage receptacles, and more particularly, to a system and method for calibrating or confirming the orientation of slides within a slide storage receptacle.

BACKGROUND

Various devices have been used to store glass slides, such as microscope and patient test slides. One known storage receptacle is a slide cassette. A cassette typically includes a pair of trays or support members or fingers that extend from the cassette and below a slot. A slide fits into a slot and onto a tray. Each slot receives a single slide. The dimensions of a slot are typically larger than the dimensions of a slide so that the slide can be easily inserted into and removed from the slot.

Automated or semi-automated imaging systems use robotic actuators or other devices to remove a slide from the cassette, process the slide or specimen, and return the slide into the cassette. For example, one device may acquire a slide from a cassette and position it beneath a microscope or other device so a cytotechnologist can analyze the sample for cancer and other medical conditions. More specifically, the imaging system grasps the slide, lifts it above the retaining members of the trays, removes the slide from the trays and the slot, and positions the slide beneath the microscope. The imaging system re-inserts the slide into the cassette after the analysis is completed.

The manner in which imaging systems and other devices check the orientation of slides in a slide cassette can be improved. Ideally, all of the slides are properly arranged flat on the trays inside the cassette and in a similar manner. However, as a result of human or machine errors, slides may be improperly loaded into a cassette. For example, a slide may be inserted upside down so that surface with a specimen sample is facing downward, whereas other slides may have their specimen samples facing upward. Further, slides can be twisted around. In other words, the slide may be inadvertently rotated 180 degrees. This may present a problem when, for example, a bar code or other data is present on one end of a slide. Slides may also be twisted and flipped upside down. Slides that are improperly loaded may cause complications with the processing equipment and processing errors, resulting in system downtime and requiring a cytotechnologist or technician to examine the cassette and rearrange slides.

Accordingly, there exists a need for a system and method that checks or provides an indication of the arrangement of slides in a cassette to ensure that all of the slides are properly loaded in the cassette. Such a system and method would improve the performance of processing equipment, safety, throughput and operator convenience.

SUMMARY

In accordance with one embodiment, a system for determining whether a slide is loaded properly within a slide receptacle includes a slide having a transparent region and a non-transparent region, a light source and a sensor. The slide is positioned between the light source and the sensor. The slide is properly loaded in the slide receptacle when the sensor detects light from the light source that passes through the transparent region of the slide.

In accordance with an alternative embodiment, a system for determining whether a plurality of slides are loaded properly in a slide receptacle includes a plurality of slides, each having a transparent region and a non-transparent region, a light source and a sensor. The slides are positioned between the light source and the sensor and are properly loaded in the slide receptacle when the sensor detects light from the light source that passes through aligned transparent regions of the slides.

In a further alternative embodiment, a system for determining whether slides are loaded properly within a slide receptacle includes a plurality of slides, each having a transparent corner region and three non-transparent corner regions, a light source and a sensor. The slides are positioned between the light source and the sensor and are properly loaded in the slide receptacle when the sensor detects light from the light source that passes through aligned transparent corner regions of the slides.

In various embodiments, a corner of a slide can have a transparent region, and the other three corners can have non-transparent corner regions, such as opaque or frosted regions that are absorptive or reflective. Different configurations, shapes, numbers, and sizes of transparent and non-transparent regions can be used. For example, the slides being arranged in a vertical stack or horizontally, and between a light source and a sensor. A transparent region can be bounded by an edge of the slide and a non-transparent region. Further, a transparent region can have a triangular, rectangular, square, circular or semi-circular shape. Each slide can have, for example, three non-transparent regions, which can be various shapes, such as triangle or rectangle shapes. The transparent and non-transparent regions may or may not be the same shape.

Also in various embodiments, the light source, such as a laser, can generate light at various wavelengths, including visible and non-visible wavelengths. The sensor can generate a signal or data that indicates whether the one or more slides are properly loaded in the slide receptacle, which can be used to generate a message that is displayed on a display screen or to activate a light or speaker

BRIEF DESCRIPTION OF THE DRAWINGS

A more complete understanding of embodiments and the advantages thereof may be acquired by referring to the following description, taken in conjunction with the accompanying drawings in which like reference numbers indicate like features and wherein:

FIG. 5 illustrates a slide having transparent and non-transparent regions for use in various embodiments;

FIG. 10 illustrates an alternative arrangement of a square shaped transparent region and non-transparent regions for use in alternative embodiments;

FIG. 11 illustrates a further alternative arrangement of a rectangular shaped transparent region and non-transparent regions for use in alternative embodiments;

FIG. 12 illustrates a further alternative arrangement of a partial circle shaped transparent region and non-transparent regions for use in alternative embodiments;

DETAILED DESCRIPTION OF ILLUSTRATED EMBODIMENTS

In the following description, reference is made to the accompanying drawings which form a part hereof, and which show by way of illustration specific embodiments. It is to be understood that structural changes may be made without departing from the scope of embodiments.

Figure 2:
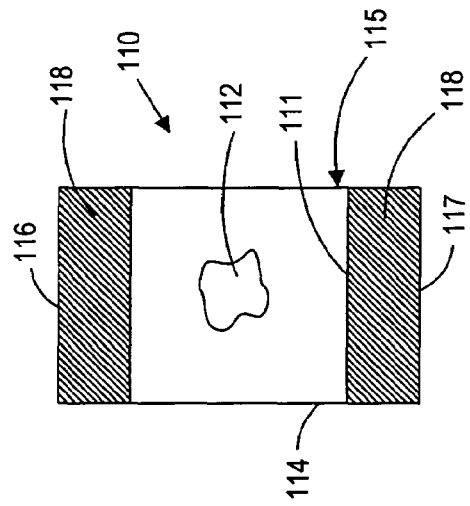
FIG. 2 is a top view of a known slide having sides that are longer than front faces or edges and having frosted end sections.
Figure 4:
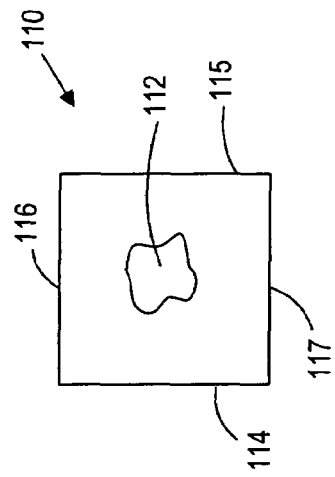
FIG. 4 is a top view of a known square-shaped slide.
Figure 1:
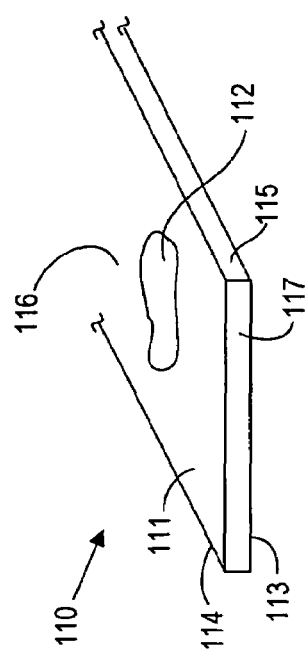
FIG. 1 is a perspective view of a known slide having sides that are longer than front faces or edges.
Figure 3:
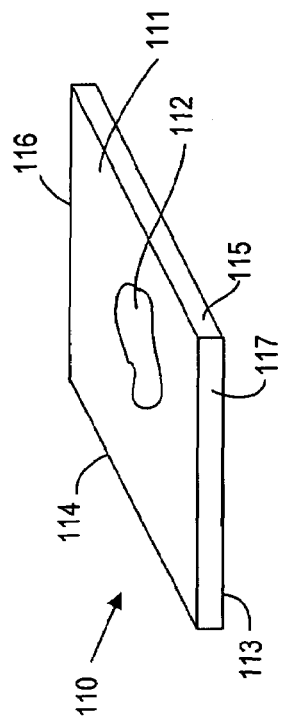
FIG. 3 is a perspective view of a known square-shaped slide having sides or edges that are the same length.

Embodiments can be utilized to determine whether slides are properly loaded or arranged within a slide receptacle, such as a cassette, such as a part no. 70292-000, available from Cytyc Corporation, 250 Campus Drive, Marlborough, Mass. 01752. As shown in FIG. 1, one exemplary slide 110 has top surface 111 with a test sample or specimen 112, a bottom surface 113, a first side 114, a second or opposite side 115, a first edge 116 that is placed within a slot 102, and a second or opposite edge 117. Referring to FIG. 2, some slides may also have frosted sections 118, which can be used to facilitate printing numbers on to the slide 110 or to identify sections of the slide 110 that should be handled. The slides shown in FIGS. 3 and 4 are generally rectangular-shaped slides, having sides 114 and 115 that are longer than edges 116 and 117. Persons skilled in the art will appreciate that other slide configurations can be utilized. For example, referring to FIGS. 3 and 4, another exemplary slide 110 is a square-shaped slide having sides 114 and 115 and edges 116 and 117 that are the same length. For purposes of illustration and explanation, not limitation, this specification refers to rectangle-shaped slides.

In normal use, slides 110 are loaded into a cassette so that they are flat and are properly positioned so that they face upright with the specimen samples 112 being on top surfaces 111 of the slides 110. All of the slides are typically arranged in a similar manner since processing equipment is typically configured to handle slides that are oriented in a particular manner. Persons skilled in the art will appreciate that the "common" orientation can vary depending on the cassette and equipment configurations, however, this specification refers to slides being flat with the specimen sample (if a specimen has been applied to a slide) facing upwardly and one end of the slide being inserted into the cassette first. Sometimes however, slides 110 are improperly placed in a cassette 100 by being flipped upside down or rotated 180 degrees so that they are not correctly arranged in the cassette. Embodiments can be used to determine whether any slides are improperly loaded or arranged in the cassette by using a transparent region.

More particularly, referring to FIG. 5, a slide 500 for use in various embodiments includes a transparent region 520 at one of the corners of the slide, and non-transparent regions 510, 512 and 514 (generally 510). In the illustrated embodiment, the non-transparent regions 510 and 512 are triangular and about the same size as the transparent region 520, however, embodiments are not so limited. In the illustrated embodiment, the non-transparent region 514 extends between the sides of the slide 500. The transparent region 520 is bounded by an edge of the slide 500 and the non-transparent region 514.

As shown in FIG. 5, the transparent region 520 is a portion of the slide 500 itself, and the non-transparent regions 510 may be, for example, portions of the slide 500 that are frosted 518 or coated with an opaque material. Alternatively, non-transparent regions 510 may be formed using other techniques, such as applying a non-transparent adhesive to the slide or treating the slide so that one portion is more transparent than the other using, for example, laser etching, polishing, or other suitable techniques. The non-transparent regions 510 may be absorptive or reflective depending on the material of the slide and the material of the non-transparent region 510 and manner of making the non-transparent region 510. For purposes of explanation, not limitation, this specification refers to non-transparent regions 510 being frosted. Frosting materials and techniques for formed a frosted, non-transparent section 518 are known in the art and are, therefore, not discussed here in further detail.

Persons skilled in the art will appreciate that non transparent regions 510 may not absorb or reflect 100% of the incident light, and that non-transparent regions 510 may transmit a small amount of light. Accordingly, references to "non-transparent" in this specification are intended to include regions that are truly non-transparent and regions that are sufficiently less transparent than a transparent region 520 to enable a sensor to detect and distinguish light passing through a transparent region 520 and any light passing through a non-transparent region 510. Whether non-transparent regions 510 having different transmission capabilities can be used may depend on, for example, the sensitivity of the sensor and the abilities of the sensor to distinguish light of different intensities.

Figure 6:
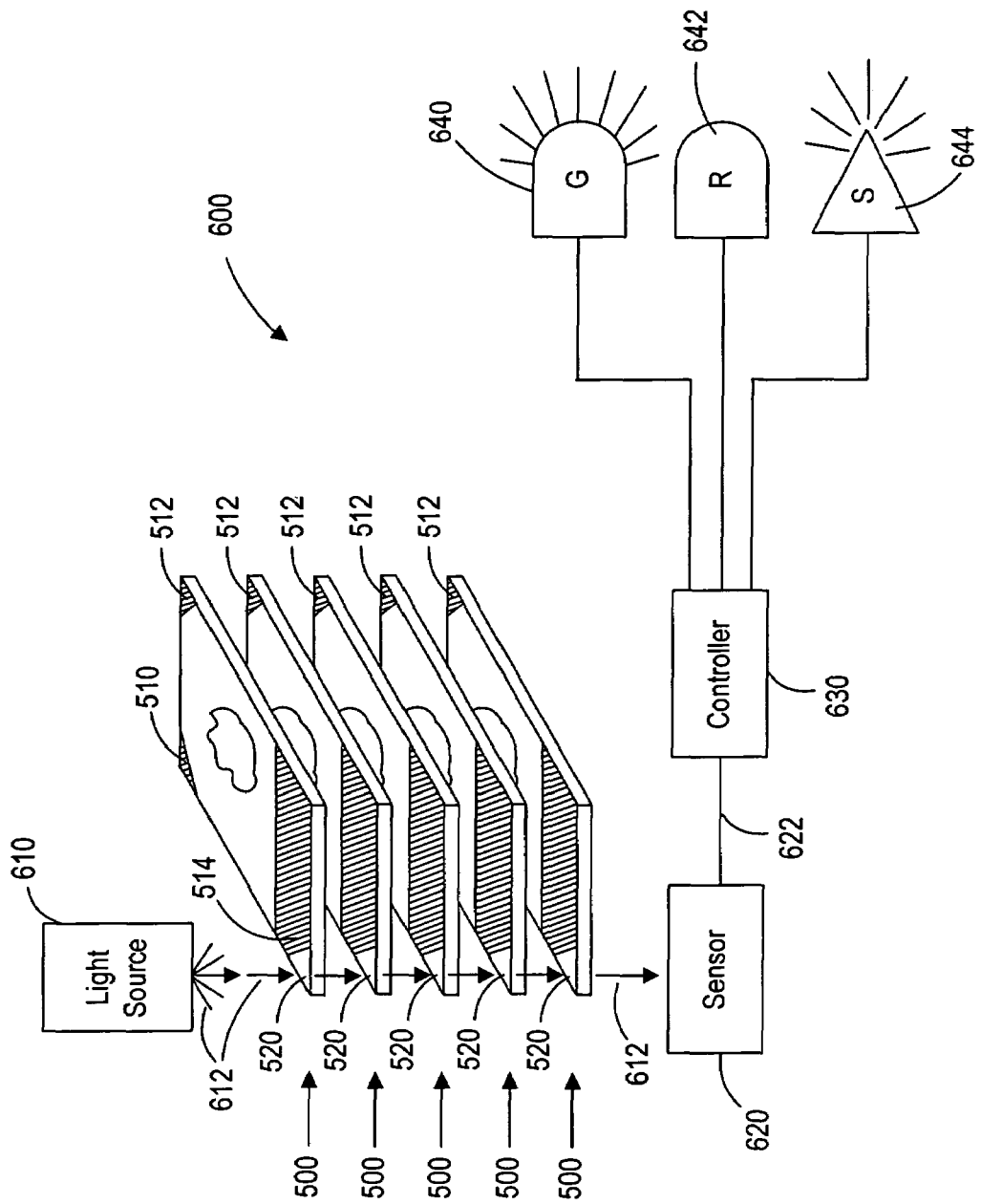
FIG. 6 illustrates a system having slides having aligned transparent sections as a result of all of the slides being properly loaded.

Referring to FIG. 6, a system 600 that includes one or more slides 500, a light source 610 that emits light or electromagnetic energy 612 and a sensor 620 that detects light 612 from the light source 610. The Figures illustrates five slides, however, persons skilled in the art will appreciate that the system can include different numbers of slides, e.g., one slide, 10 slides, 50 slides, etc.

The type of light source 610 that is used can depend on the type of slides or the slide 500 material, the number of slides 500, the strength of the light source 610 and the sensitivity of the sensor 620. Exemplary light sources 610 include a white light source, a Light Emitting Diode (LED) and a laser. Light 612 from the light source 610 may be collimated, and may be of various wavelengths, including visible wavelengths raging from about 400 nanometers (nm) to about 700 nm, and invisible wavelengths, such as infrared wavelengths of about 700 nm to about 1000 nm, and ultraviolet wavelengths of about 100 nm to about 400 nm. One exemplary light source 610 and sensor 620 combination is Model LDM-5 low dispersion laser module, available from Laserex Technologies Pty Ltd., 5a Corbett Court, Export Park, SA 5950, Australia, that emits light at wavelengths of about 635, 650, 670, 780, 808, 830 and 850 nm, and a Model LR-4 analogue receiver, also available from Laserex, having a bandwidth range of about 350-1100 nm. Persons skilled in the art will appreciate that other light source and sensors can also be utilized.

In the illustrated embodiment, the slides 500 are shown as a vertical stack as they would be arranged in a slide cassette. In this embodiment, the light source 610 and sensor 620 are positioned at opposite ends of the slides 500, i.e., above and below the vertical stack. The light source 610 and sensor 620 may also be switched so that the sensor 620 is above the stack of slides 500 and the light source 610 is below the slides 500. Thus, embodiments can be used with different arrangements of slides.

The system or a user can determine whether the slides 500 are properly loaded in the cassette based on whether light 612 from the light source 610 passes through the transparent regions 520 of all of the slides 500 and is detected by the sensor 620, as shown in FIG. 6. This is possible when none of the non-transparent regions 510 are located within the path of the light 612, thus allowing the light 612 to pass through the transparent regions 520 to the sensor 620.

The sensor 620 generates data or a signal 622 that can be used to provide an indication whether the sensor 620 has detected light 612 from the light source 610, i.e., whether the slides are properly loaded in the cassette. The sensor signal 622 or additional components can be used to provide indication functions. For example, the sensor output 622 can drive the indicator directly, or the sensor output 622 can be provided to a controller 630, such as a micro-processor, micro-controller, or logic circuitry or gates, which provides the necessary data or signal 632 to activate one or more indicators, as shown in FIG. 6, to provide a pass/fail indication. Further, the controller 630 can be used to initiate other actions or displays. For example, the controller 630 can generate a signal or data that is used by the controlling system or computer which, in response to the signal or data, generates an error message that is displayed on a screen. Alternatively, the computer can initiate corrective action, if the system is so configured.

Indicators that can be used include a visual indicator, an audible indicator, or a combination thereof. For example, a visual indicator can be an indicator light or Light Emitting Diode (LED), such as LEDs 640 and 642. An audible indicator can be a speaker (S) 644. In the illustrated embodiment, the indicators include two LEDs 640 and 642 and one speaker 644. The LED 640 is a green (G) LED to indicate that the slides are all properly loaded and aligned within the cassette and that processing can continue. The LED 642 is a red (R) LED to indicate that the one or more slides are not properly loaded in the cassette and that the cassette requires maintenance to correct the slide alignment. Persons skilled in the art will appreciate that other indication color schemes or information can also be utilized.

If the slides 500 are properly loaded in the cassette, as shown in FIG. 6, all of the transparent regions 520 are aligned with each other. In this arrangement, light 612 is detected by the sensor 620, and the sensor 620 or controller 630 provides an appropriate signal to drive an indicator, such as the green LED 640 and or speaker 644, to indicate that the slides are properly loaded and the cytotechnologist can proceed.

On the other hand, if the slides 500 are not properly loaded, then the sensor 620 or controller 630 does not detect light 612 and can generate signals to activate the red LED 642 and/or speaker 644, to indicate that one or more slides are improperly loaded, thus requiring the cytotechnologist's attention. The signal 632 can be generated based on, for example, the absence of light 612 being detected within a pre-determined amount of time after the slides are loaded or after a request of a user to check the arrangement of slides in the cassette.

Figure 7:
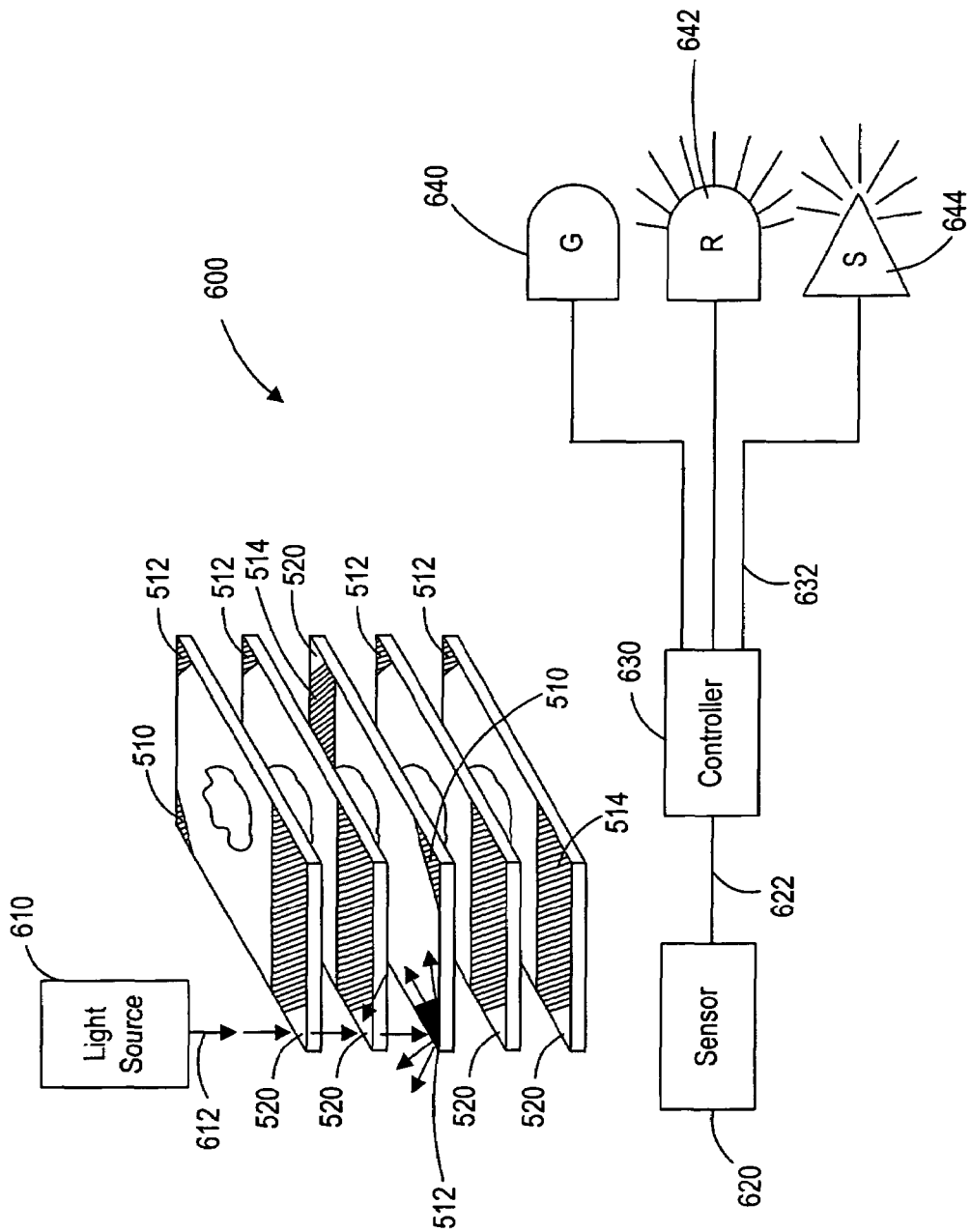
FIG. 7 illustrates a system having slides having misaligned transparent sections due to a slide being rotated end to end.
Figure 8:
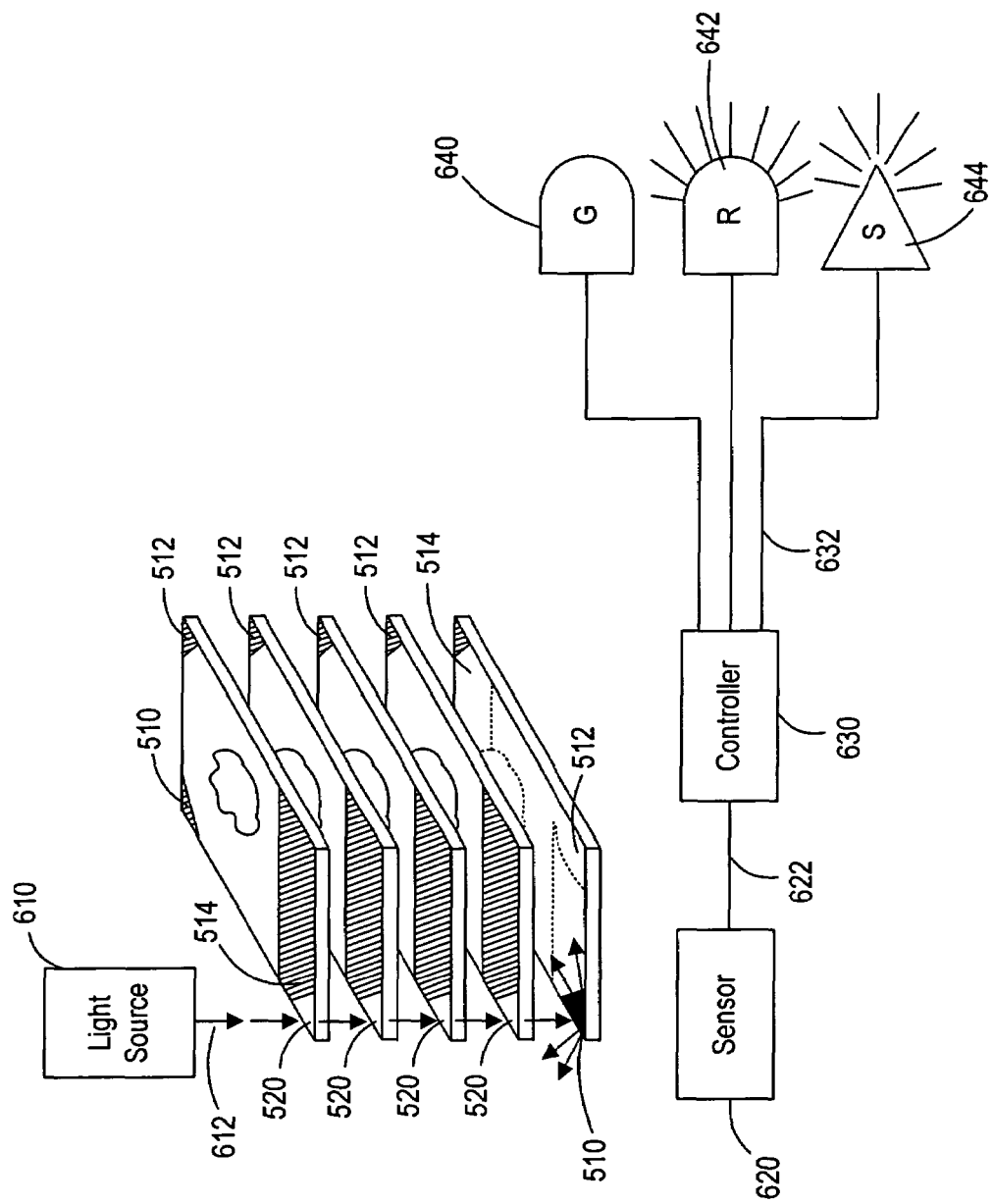
FIG. 8 illustrates a system having slides having misaligned transparent sections due to a slide being flipped upside down.

FIGS. 7 and 8 illustrate possible arrangements in which one or more slides are misloaded. In particular, FIG. 7 shows a slide being rotated 180 degrees so that the wrong end is loaded into the cassette. In this arrangement, the top two and the bottom two slides 500 are properly loaded, but the middle slide 500 is improperly rotated. As a result, non-transparent regions 510 and 512 are rotated around, and the transparent region 520 is located inside the cassette rather than being located within the path of the light 612 if the slide were properly loaded. Consequently, light 612 from the light source 610 is absorbed or reflected by non-transparent region 512 and does not reach the sensor 620. The sensor 620 or controller 630 generates an indication that one or more slides are improperly loaded, thus requiring the cytotechnologist's attention.

FIG. 8 shows another arrangement in which a slide is improperly loaded. In this example, the bottom slide of the stack is flipped upside down. As a result, non-transparent regions 510 and 512 are flipped and are still located inside the cassette. The non-transparent region 514 is now in the path of the light 612, and the transparent region 520 is now outside of the path of the light 612. As a result, light 612 from the light source 610 is absorbed or reflected by non-transparent region 514 and does not reach the sensor 620. The sensor 620 or controller 630 generates an indication that one or more slides are improperly loaded, thus requiring the cytotechnologist's attention. Further, a slide may also be flipped and rotated, which is essentially a combination of the arrangements shown in FIGS. 7 and 8. This arrangement would also result in a non-transparent section blocking the light and causing an indication to be generated that one or more slides are not properly loaded in the cassette.

Figure 9:
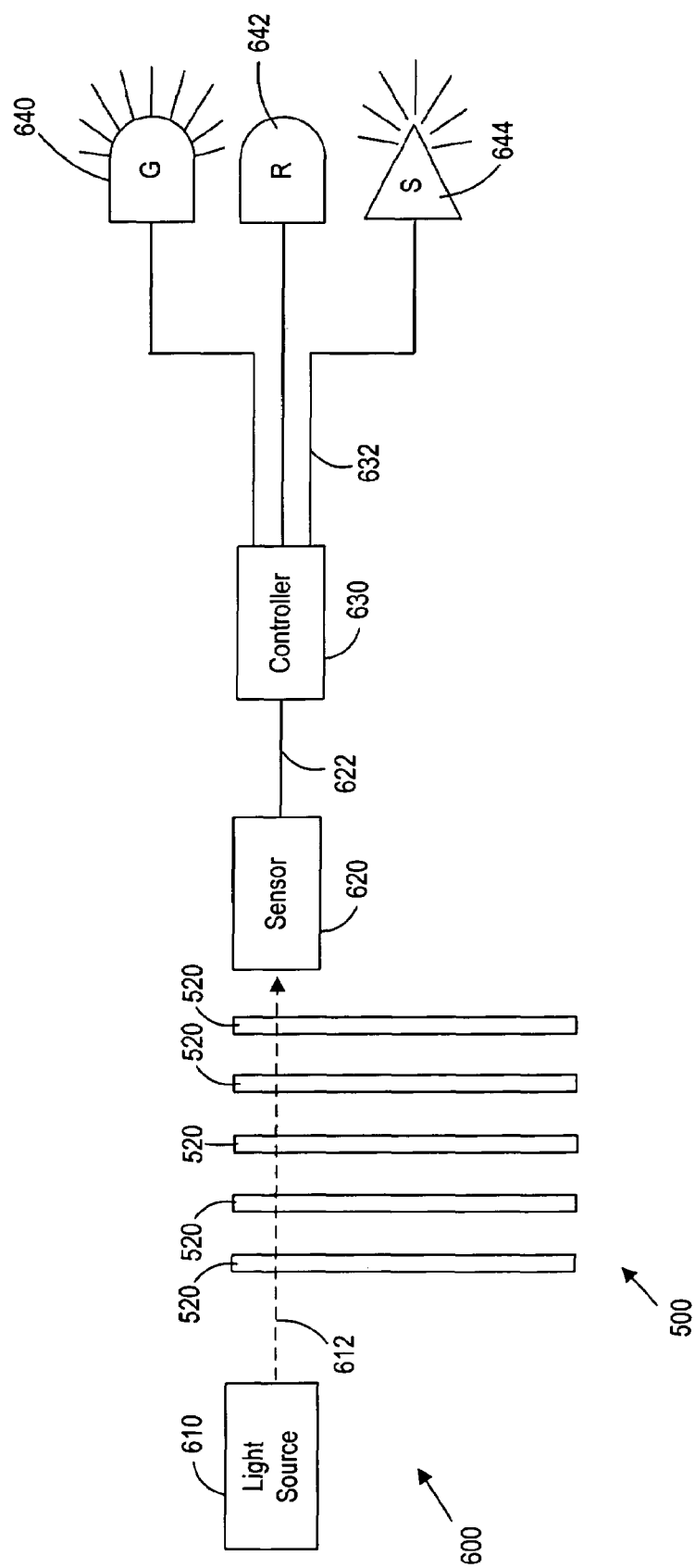
FIG. 9 illustrates a system having slides that are arranged on a slide or edge and having aligned transparent sections.

Persons skilled in the art will appreciate that alternative embodiments include the use of different transparent and non-transparent patterns, light sources, sensors, slide materials and slide arrangements. For example, in the embodiments illustrated in FIGS. 6-8, slides 500 are shown in their representative arrangement in a cassette, i.e., stacked vertically and spaced apart from each other. In an alternative embodiment, slides 500 may be stacked on top of each other so each slide contacts another slide. Moreover, as shown in FIG. 9, the system 600 can be configured to perform the same functions with slides 500 that are arranged horizontally or on a side or edge.

Different patterns of transparent and non-transparent regions can also be used. For example, although FIGS. 5-8 illustrate slides 500 with triangle-shaped transparent region 520 located at a corner of a slide, the transparent region 520 can have other shapes and sizes. For example, FIG. 10 illustrates a slide 1000 having a square-shaped transparent region 1020 partially surrounded by a non-transparent region 1014. The non-transparent regions 1010 and 1012 can be about the same shape and size as the transparent region 1020. FIG. 11 illustrates a slide 1100 having a rectangle-shaped transparent region 1120 that is partially surrounded by a non-transparent region 1114. The non-transparent regions 1110 and 1112 can be about the same shape and size as the transparent region 1120. FIG. 12 illustrates a slide 1200 having a semi-circle shaped transparent region 1220 that is partially surrounded by a non-transparent region 1214. The non-transparent regions 1210 and 1212 can, be about the same shape and size as the transparent region 1220 or, as shown in FIG. 12, be other shapes and/or sizes so that the non-transparent regions 1210 and 1212 may block light 612 from the light source 610.

Figure 15:
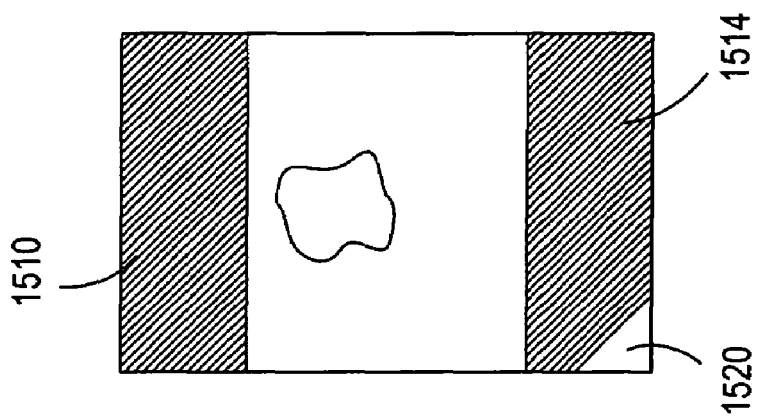
FIG. 15 illustrates a further alternative arrangement of a transparent region and a non-transparent region at the opposite end and extending between the sides of the slide.
Figure 14:
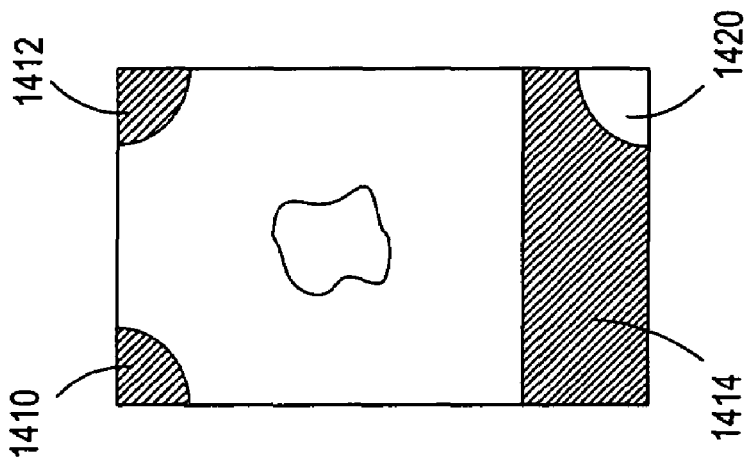
FIG. 14 illustrates another alternative arrangement of a partial circle transparent region at an opposite side relative to FIG. 12 and surrounded by a non-transparent regions for use in alternative embodiments.
Figure 13:
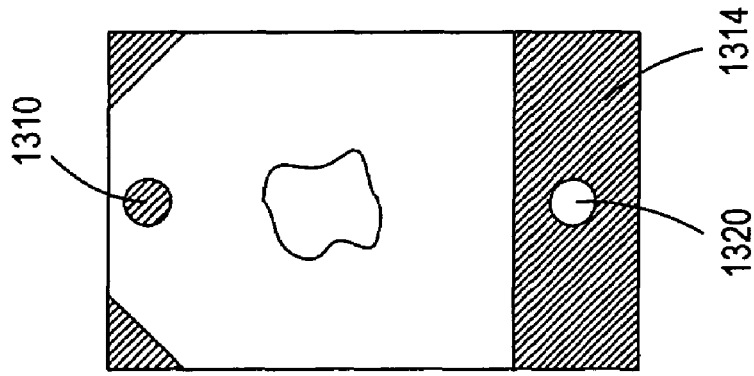
FIG. 13 illustrates another alternative arrangement of a circular transparent region surrounded by a non-transparent regions for use in alternative embodiments.

FIGS. 13-15 further illustrate how the transparent and non-transparent regions can be different shapes and/or sizes to suit different applications. For example, as shown in FIG. 13, the transparent region 1320 is no longer bounded by an edge of the slide and a non-transparent region. Rather, the transparent region 1320 in the illustrated embodiment is circular in shape (or another shape) and surrounded by a non-transparent region 1314. The slide 1300 also includes a non-transparent region 1310 that in the shape of a circle (or another shape) so that light 612 that normally passes through the transparent region 1320 would be blocked by the non-transparent region 1310 if the slide is not loaded properly in the cassette.

As a further example, the transparent region 1420 can be located along the other edge of the slide, as shown in FIG. 14. In this embodiment, the non-transparent region 1414 partially surrounds the transparent region 1420, and the non-transparent regions 1410 and 1412 are about the shape and size as the transparent region 1420. As a further example, as shown in FIG. 15, the transparent region 1520 can be a triangle-shaped transparent region that is surrounded by a non-transparent region 1514, similar to the configuration shown in FIG. 15. At the opposite end of the slide, however, the entire end of the slide can be non-transparent 1510 rather than using separate non-transparent regions as shown in other figures since both configurations would block light 612 from the light source 610 if the slide is not properly loaded into the cassette.

Persons skilled in the art will appreciate that various combinations of rectangular, square, circular, and other shapes of transparent and non-transparent regions can be used to allow light to pass through the transparent region in one arrangement of a slide and to be blocked by a non-transparent region in another arrangement of the slide. Shapes of the transparent region and the non-transparent regions may or may not match. The sizes of the non-transparent regions can also vary as needed. As further example, the entire end of the slide can be a non-transparent regions since the slides still include a common transparent region. Moreover, the transparent regions may be different sizes. The shape and size of the transparent regions may depend on, for example, the size of the slide, and the light source that is used, e.g., whether the light source is a collimated light source or a diffuse light source, since collimated light sources may be used with both larger and smaller sized transparent regions. Additionally, the transparent region and corresponding non-transparent region(s) may be occupy different locations on a slide. Further, the transparent section may be bounded by an edge of the slide and a non-transparent region or may be surrounded by a non-transparent region. Accordingly, the configurations shown in FIGS. 10-15 are provided as illustrative embodiments, and are not intended to be limiting.

Accordingly, persons skilled in the art will appreciate that there are various numbers, shapes, sizes, and positions of transparent and non-transparent regions that provide an indication of a unique arrangement of transparent regions light passes from the light source through the aligned transparent regions to the sensor to indicate, in which case the slides are properly loaded in the cassette.

Moreover, embodiments can be used with different numbers of slides, e.g., one, two, three, twenty or one hundred slides. Thus, the illustrative examples that include five slides are not intended to be limiting. If necessary, the types of light sources and detectors can be selected so that they can be used with different numbers of slides, different light intensities, and different sensor sensitivities since the quantity of light that passes through different numbers of slides may vary, thus requiring different sensitivity capabilities when detecting the light. Additionally, although this specification primarily refers to glass slides, other slide materials may also be utilized, such as plastic slides. The types of light sources and detectors can also be selected based on the transmission capabilities of the slide material. Although references have been made in the foregoing description to various embodiments, persons skilled in the art will recognize that insubstantial modifications, alterations, and substitutions can be made to the described embodiments without departing from the invention as claimed in the accompanying claims.

The invention claimed is:

1. A system for determining whether slides are loaded properly in a slide receptacle, comprising:
   a plurality of slides, each slide having a transparent region that is a portion of the slide and a non-transparent region;
   a light source; and
   a sensor, the slides being between the light source and the sensor, the slides being properly loaded in the slide receptacle when the sensor detects light from the light source that passes through aligned transparent regions of the slides.

2. The system of claim 1, the transparent region being a transparent corner region.

3. The system of claim 1, the transparent region being bounded by an edge of the slide and a non-transparent region.

4. The system of claim 1, the transparent region having a triangular, a rectangular, a square, a circular or a semi-circular shape.

5. The system of claim 1, the non-transparent region being opaque.

6. The system of claim 1, the non-transparent region being frosted.

7. The system of claim 1, the non-transparent region being absorptive.

8. The system of claim 1, the non-transparent region being reflective.

9. The system of claim 1, the transparent region and the non-transparent region having the same shape.

10. The system of claim 1, the light source being a laser.

11. The system of claim 1, the sensor generating a signal or data indicating whether the plurality of slides are properly loaded in the slide receptacle based on whether the sensor detects light from the light source that passes through aligned transparent regions.

12. The system of claim 1, the light source and the sensor being arranged substantially perpendicular to top and bottom surfaces of the plurality of slides.

13. The system of claim 1, the slides being arranged in a vertical stack.

14. The system of claim 1, the slides being arranged horizontally.

15. The system of claim 1, the plurality of slides being improperly loaded in the slide receptacle when light from the light source is blocked by a non-transparent region.

16. The system of claim 1, wherein the plurality of slides and the transparent regions are glass.

17. A system for determining whether slides are loaded properly within a slide receptacle, comprising:
- a plurality of slides, each slide having a transparent corner region that is a portion of the slide and three non-transparent corner regions;
- a light source; and
- a sensor, the slides being between the light source and the sensor, the slides being properly loaded in the slide receptacle when the sensor detects light from the light source that passes through aligned transparent corner regions of the slides.

18. The system of claim 17, the transparent corner region being bounded by an edge of the slide and a non-transparent region.

19. The system of claim 17, the transparent corner region having a triangular, a rectangular, a square, a semi-circular or a circular shape.

20. The system of claim 17, the non-transparent corner region being opaque.

21. The system of claim 17, the non-transparent corner region being frosted.

22. The system of claim 17, the non-transparent corner regions being absorptive.

23. The system of claim 17, the non-transparent corner regions being reflective.

24. The system of claim 17, the transparent region and the non-transparent region having the same shape.

25. The system of claim 17, the light source being a laser.

26. The system of claim 17, the sensor generating a signal or data indicating whether the plurality of slides are properly loaded in the slide receptacle based on whether the sensor detects light from the light source that passes through aligned transparent regions.

27. The system of claim 17, the slides being arranged in a vertical stack.

28. The system of claim 17, the slides being arranged horizontally.

29. The system of claim 17, the plurality of slides being improperly loaded in the slide receptacle when light from the light source is blocked by a non-transparent corner region.

30. The system of claim 17, wherein the plurality of slides and the transparent regions are glass.

31. A system for determining whether a specimen slide is loaded properly within a slide receptacle, comprising:
- a specimen slide having a transparent region that is a portion of the specimen slide and a non-transparent region;
- a light source; and
- an optoelectronic sensor, the slide being positioned between the light source and the sensor, the specimen slide being properly loaded in the slide receptacle when the sensor detects light from the light source that passes through the transparent region of the specimen slide.

32. The system of claim 31, wherein the specimen slide and the transparent region are glass.

33. The system of claim 31, further comprising:
- a controller connected to an output of the sensor; and
- an indicator connected to an output of the controller, the controller being configured to activate the indicator to indicate whether the specimen slide is properly loaded within the slide receptacle.

34. The system of claim 33, wherein the controller is a microprocessor, a micro-controller or logic circuitry.

35. The system of claim 31, further comprising a visual or audible indicator connected to an output of the sensor, the sensor being configured to activate the indicator to indicate whether the specimen slide is properly loaded within the slide receptacle.

36. A system for determining whether slides are loaded properly in a slide receptacle, comprising:
- a plurality of slides, each slide having a transparent region and a non-transparent region, the transparent region being bounded by an edge of the slide and a non-transparent region;
- a light source; and
- a sensor, the slides being between the light source and the sensor, the slides being properly loaded in the slide receptacle when the sensor detects light from the light source that passes through aligned transparent regions of the slides.

37. A system for determining whether slides are loaded properly within a slide receptacle, comprising:
- a plurality of slides, each slide having a transparent corner region and three non-transparent corner regions, the transparent corner region being bounded by an edge of the slide and a non-transparent region;
- a light source; and
- a sensor, the slides being between the light source and the sensor, the slides being properly loaded in the slide receptacle when the sensor detects light from the light source that passes through aligned transparent corner regions of the slides.

* * * * *